US012672634B2

(12) United States Patent
Trees

(10) Patent No.: US 12,672,634 B2
(45) Date of Patent: Jul. 7, 2026

(54) *LANTANA CAMARA* CULTIVAR 'BALLANPAF'

(71) Applicant: Ball Horticultural Company, West Chicago, IL (US)

(72) Inventor: Scott C. Trees, Arroyo Grande, CA (US)

(73) Assignee: Ball Horticultural Company, West Chicago, IL (US)

( * ) Notice: Subject to any disclaimer, the term of this patent is extended or adjusted under 35 U.S.C. 154(b) by 629 days.

(21) Appl. No.: 18/111,193

(22) Filed: Feb. 17, 2023

(65) Prior Publication Data

US 2024/0276941 A1 Aug. 22, 2024

(51) Int. Cl.
*A01H 5/02* (2018.01)
*A01H 6/86* (2018.01)

(52) U.S. Cl.
CPC ................ *A01H 6/86* (2018.05); *A01H 5/02* (2013.01)

(58) Field of Classification Search
CPC ...................................................... A01H 6/86
USPC ......................................................... 800/323
See application file for complete search history.

(56) References Cited

U.S. PATENT DOCUMENTS

PP29,653 P2 9/2018 Pan

OTHER PUBLICATIONS

Tsuda et al., Construction of a high-density mutant library in soybean and development of a mutant retrieval method using amplicon sequencing, BMC Genomics 16: 1014, pp. 1-18 (Year: 2015).*
Greenhouse Grower's. Greenhouse Grower's 2023 Readers' Choice Award. Accessed on Jun. 7, 2023. Retrieved from: <https://www.greenhousegrower.com/readerschoice/>.
Sanders. "The Genera of Verbenaceae in the Southeastern United States". Harvard Papers in Botany, vol. 5(2), 2001, pp. 303-358.
Scheper. "Floridata Plant Profile; #59 Lantana camara", last updated Nov. 16, 2004. Accessed from <https://floridata.com/plant/59>.
Veraplakorn et al., "Micropropagation and callus induction of Lantana camara L.—A medicinal plant". Agriculture and Natural Resources (2016), 50(5); 338-344.

* cited by examiner

*Primary Examiner* — Li Zheng
(74) *Attorney, Agent, or Firm* — Dentons US LLP

(57) ABSTRACT

The invention provides plants of the *Lantana camara* cultivar designated 'Ballanpaf'. The invention thus relates to the plants, cells, plant parts, and tissue cultures of the cultivar 'Ballanpaf', and to methods for producing a *Lantana camara* plant produced by crossing a *Lantana camara* plant of cultivar 'Ballanpaf' with another lantana plant, such as a plant of another cultivar. The invention further relates to *Lantana camara* seeds and plants produced by crossing plants of cultivar 'Ballanpaf' with plants of another cultivar. The invention further relates to the genetic complements and hybrid genetic complements of plants of cultivar 'Ballanpaf'.

25 Claims, 2 Drawing Sheets

*LANTANA CAMARA* CULTIVAR 'BALLANPAF'

FIELD OF THE INVENTION

The present invention relates to the field of plant breeding and, more specifically, to *Lantana camara* plants having attractive flower coloration, dark green colored foliage, and a trailing growth habit suitable for hanging baskets. In particular, the invention relates to plants of the cultivar designated 'Ballanpaf', and derivatives and tissue cultures thereof.

DESCRIPTION OF RELATED ART

*Lantana camara*, commonly known as lantana, is a member of the Verbenaceae family. See, e.g., Sanders, R. W. (2001) The Genera of Verbenaceae in the Southeastern United States. Harvard Papers in Botany. Vol. 5, No. 2, pages 303-358. The shrub-like plant, can grow to 6 ft. in height and 8 ft. in width in tropical conditions, providing long-lasting color in mixed beds and borders. The species is native to Central and South America and has become naturalized nearly throughout the tropics as well as southern and southwestern regions of the United States (See, e.g. "*Lantana camara*". Floridata L C. 2007; https://floridata.com/plant/59)

The inflorescences are known to attract birds and insects. Because the species can tolerate stressful climatic conditions, including drought and salt sprays, plants are useful for xeriscapes and the beach ornamental plantings. Although the species is typically hardy only to Zone 8, it is fast growing making it a valued annual in colder regions for use in bedding, hanging basket, and container plantings.

Lantana is extremely easy to grow requiring little attention and is seldom bothered by pests or disease. It has low water requirements and can be used in xeriscapes and can handle the heat growing in containers and hanging baskets under sunny conditions. An ornamental *Lantana* having a more trailing habit for hanging basket use is desirable in the marketplace.

SUMMARY OF THE INVENTION

In one aspect, the invention provides a *Lantana camara* plant of cultivar 'Ballanpaf'. Also provided are seeds and plants having all of the physiological and morphological characteristics of such plants. Parts of these *Lantana camara* plants are also provided, for example, including a flower, pollen, a leaf, an ovule, an embryo, a cutting, an axillary bud, a stem, or a seed, and a cell of the plant.

In another aspect of the invention, a tissue culture of regenerable cells of *Lantana camara* cultivar 'Ballanpaf' is provided. The tissue culture will preferably be capable of regenerating *Lantana camara* plants capable of expressing all of the physiological and morphological characteristics of the starting plant and of regenerating plants having substantially the same genotype as the starting plant. Examples of some of the physiological and morphological characteristics of *Lantana camara* cultivar 'Ballanpaf' include those traits set forth in the phenotypic description provided herein. The regenerable cells in such tissue culture may be derived, for example, from embryos, meristems, cotyledons, pollen, leaves, anthers, roots, root tips, pistils, flowers, cuttings, seeds, and stems. Still further, the present invention provides *Lantana camara* plants regenerated from a tissue culture of the invention, the plants having all of the physiological and morphological characteristics of *Lantana camara* cultivar 'Ballanpaf'.

In another yet another aspect, the invention provides a method of vegetatively propagating a *Lantana camara* plant comprising the steps of: (a) collecting tissue capable of being propagated from a plant of *Lantana camara* cultivar 'Ballanpaf'; and (b) propagating a plant from said tissue. The method will preferably be capable of producing *Lantana camara* plants capable of expressing all of the physiological and morphological characteristics of the starting plant and of producing plants having substantially the same genotype as the starting plant. Still further, the present invention provides *Lantana camara* plants produced by vegetative propagation of *Lantana camara* cultivar 'Ballanpaf'. In some embodiments, such plants have all of the physiological and morphological characteristics of *Lantana camara* cultivar 'Ballanpaf'.

In one aspect, a plant of *Lantana camara* cultivar 'Ballanpaf' further comprising an added heritable trait is provided. In some embodiments, the heritable trait may comprise a transgene or may comprise a genetic locus that is, for example, a dominant or recessive allele. In specific embodiments, the added genetic locus may confer one or more traits, such as for example, herbicide tolerance, pest resistance, or disease resistance. In further embodiments, the trait may be conferred by a naturally occurring gene introduced into the genome of a line by backcrossing, a non-transgenic mutation, or a transgene introduced through genetic transformation techniques into the plant or a progenitor of any previous generation thereof. When introduced through transformation, a genetic locus may comprise one or more genes integrated at a single chromosomal location.

In another aspect, a plant of *Lantana camara* cultivar 'Ballanpaf' further comprising a single locus conversion is provided. In some embodiments, a single locus conversion includes one or more site-specific changes to the plant genome, such as, without limitation, one or more nucleotide modifications, deletions, or insertions. A single locus may comprise one or more genes or nucleotides integrated or mutated at a single chromosomal location. In one embodiment, a single locus conversion may be introduced by a genetic engineering technique, methods of which include, for example, genome editing with engineered nucleases (GEEN). Engineered nucleases include, but are not limited to, Cas endonucleases; zinc finger nucleases (ZFNs); transcription activator-like effector nucleases (TALENs); engineered meganucleases, also known as homing endonucleases; and other endonucleases for DNA or RNA-guided genome editing that are well-known to the skilled artisan. The single locus conversion may confer one or more traits, such as for example, white, yellow, yellow-orange, orange, red-orange, red, purplish-red, purplish-pink, reddish-purple, or purple flower coloring.

In yet another aspect, the invention provides a method comprising applying plant breeding techniques to a plant of *Lantana camara* cultivar 'Ballanpaf'. In some embodiments, the method comprises producing a *Lantana camara* cultivar 'Ballanpaf'-derived plant. Non-limiting examples of plant breeding techniques include recurrent selection, mass selection, hybridization, open-pollination, backcrossing, modified backcrossing, endosperm culture, pedigree breeding, mutation breeding, or marker assisted selection. In one embodiment, the method comprises selecting a *Lantana camara* cultivar 'Ballanpaf'-derived *Lantana camara* plant that comprises a trailing growth habit found in *Lantana camara* cultivar 'Ballanpaf'. In specific embodiments, a

*Lantana camara* plant produced by the breeding techniques described herein may have inflorescence comprising white, yellow, yellow-orange, orange, red-orange, red, purplish-red, purplish-pink, reddish-purple, or purple flowers.

In still yet another aspect, the present invention provides a method of obtaining a *Lantana camara* plant with deep yellow, medium orange, and deep reddish-purple multicolored inflorescences, dark green-colored foliage, and a vigorous, trailing growth habit comprising producing a progeny plant of *Lantana camara* cultivar 'Ballanpaf'.

In one aspect, the present invention provides a method of introducing a trailing growth habit into a *Lantana* plant, the method comprising the steps of: (a) crossing a plant of *Lantana camara* cultivar 'Ballanpaf' according to claim 1 with a second *Lantana* plant to produce F1 progeny; (b) selecting an F1 progeny that comprises the trailing growth habit found in *Lantana camara* cultivar 'Ballanpaf'; (c) backcrossing the selected F1 progeny with the second *Lantana* plant to produce backcross progeny; and (d) repeating steps (b) and (c) three or more times to produce a selected fourth or higher backcross progeny that comprises the trailing growth habit found in *Lantana camara* cultivar 'Ballanpaf'. In some embodiments, plants produced by such methods are also provided.

In another aspect, the present invention provides a method comprising vegetatively propagating a *Lantana camara* plant comprising a trailing growth habit found in *Lantana camara* cultivar 'Ballanpaf', wherein the plant is the product of applying a plant breeding technique to a plant of *Lantana camara* cultivar 'Ballanpaf'.

Any embodiment discussed herein with respect to one aspect of the invention applies to other aspects of the invention as well, unless specifically noted.

The term "about" is used to indicate that a value includes the standard deviation of the mean for the device or method being employed to determine the value. The use of the term "or" in the claims is used to mean "and/or" unless explicitly indicated to refer to alternatives only or the alternatives are mutually exclusive. When used in conjunction with the word "comprising" or other open language in the claims, the words "a" and "an" denote "one or more," unless specifically noted otherwise. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

Other objects, features, and advantages of the present invention will become apparent from the following detailed description. It should be understood, however, that the detailed description and any specific examples provided, while indicating specific embodiments of the invention, are given by way of illustration only, since various changes and modifications within the spirit and scope of the invention will become apparent to those skilled in the art from this detailed description.

DETAILED DESCRIPTION OF THE INVENTION

Definitions

Figure 1:
FIG. 1: Illustrates the overall growth and flowering habit of *Lantana camara* plants of the cultivar designated 'Ballanpaf'.
Figure 2:
FIG. 2: Illustrates a close-up view of an individual inflorescence of *Lantana camara* plants of the cultivar designated 'Ballanpaf'.

Allele: Any of one or more alternative forms of a gene locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny back to one of the parents, for example, a first generation hybrid ($F_1$) with one of the parental genotypes of the $F_1$ hybrid.

Crossing: The pollination of a female flower of a *Lantana camara* plant, thereby resulting in the production of seed from the flower.

Cross-pollination: Fertilization by the union of two gametes from different plants.

Diploid: A cell or organism having two sets of chromosomes.

$F_1$ Hybrid: The first generation progeny of the cross of two plants.

Genetic Complement: An aggregate of nucleotide sequences, the expression of which sequences defines the phenotype in *Lantana camara* plants, or components of plants including cells or tissue.

Genotype: The genetic constitution of a cell or organism.

Haploid: A cell or organism having one set of the two sets of chromosomes in a diploid.

Linkage: A phenomenon wherein alleles on the same chromosome tend to segregate together more often than expected by chance if their transmission was independent.

Marker: A readily detectable phenotype, preferably inherited in codominant fashion (both alleles at a locus in a diploid heterozygote are readily detectable), with no environmental variance component, i.e., heritability of 1.

Non-transgenic mutation: A mutation that is naturally occurring (spontaneous), or induced by conventional methods (e.g. exposure of plants to radiation or mutagenic compounds), not including mutations made using recombinant DNA techniques.

Phenotype: The detectable characteristics of a cell or organism in which the characteristics are the manifestation of gene expression.

Quantitative Trait Loci (QTL): Genetic loci that contribute, at least in part, certain numerically representable traits that are usually continuously distributed.

Regeneration: The development of a plant from tissue culture.

SSR profile: A profile of simple sequence repeats used as genetic markers and scored by gel electrophoresis following PCR amplification using flanking oligonucleotide primers.

Self-pollination: The transfer of pollen from the anther to the stigma of the same plant.

Single Locus Converted (Conversion) Plant: Plants that are developed by a plant breeding technique called backcrossing or by genetic engineering of a locus, wherein essentially all of the morphological and physiological characteristics of a plant are recovered in addition to the characteristics conferred by the single locus transferred into the plant via the backcrossing or genetic engineering technique.

Substantially Equivalent: A characteristic that, when compared, does not show a statistically significant difference (e.g., p=0.05) from the mean.

Tissue Culture: A composition comprising isolated cells of the same or a different type or a collection of such cells organized into parts of a plant.

Transgene: A genetic sequence that has been introduced into the nuclear or chloroplast genome of a *Lantana camara* plant by genetic transformation or site-specific modification.

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

*Lantana camara* Cultivar 'Ballanpaf'

The disclosure provides *Lantana camara* plants with deep yellow, medium orange and deep reddish-purple multicolored inflorescences, dark green-colored foliage, and a vigorous, trailing growth habit as compared other known *Lantana camara* cultivars.

A. Origin and Breeding History

*Lantana camara* cultivar 'Ballanpaf' was selected as a single flowering plant resulting from a controlled cross-pollination in Guadalupe, California in July 2017. The female (seed) parent is a proprietary *Lantana camara* breeding selection coded 18231 (not patented); and the male (pollen) parent is BANDANA Landscape Red 'LANZ0015' (U.S. Plant Pat. No. 29,653). During trials, plants of the selected cultivar were observed to comprise a combination of traits including deep yellow, medium orange and deep reddish-purple multicolored inflorescences, dark green-colored foliage, and a vigorous, trailing growth habit. This combination of traits is unique compared to all other known *Lantana camara* cultivars. In particular, the trailing habit visually exceeds that of other known cultivars, making the plant highly desirable in a hanging basket display. The selected plant was later given the cultivar name 'Ballanpaf'.

The female (seed) parent of the new cultivar is the proprietary *Lantana camara* breeding selection coded 18231, not patented, characterized by its medium pink and yellow colored inflorescences, dark green-colored foliage, and vigorous, spreading growth habit. The male (pollen) parent of the new cultivar is BANDANA Landscape Red 'LANZ0015', U.S. Plant Pat. No. 29,653, characterized by its large sized, dark yellow-orange and dark red-colored inflorescences, medium green-colored foliage, and vigorous, spreading growth habit. *Lantana camara* cultivar 'Ballanpaf' differs from plants of its female and male parents primarily in having a more trailing growth habit and in having multicolored inflorescences that is different from both the medium pink and yellow colored inflorescences of the female parent and the dark yellow-orange and dark red colored inflorescences of the male parent.

Asexual reproduction of the new cultivar by terminal stem cuttings since May 2018 in Guadalupe, California and Arroyo Grande, California has demonstrated that the new cultivar reproduces true to type with all of the characteristics, as herein described, firmly fixed and retained through successive generations of such asexual propagation.

B. Phenotypic Description

In accordance with another aspect of the present invention, there is provided a *Lantana camara* plant having the morphological characteristics of *Lantana camara* cultivar 'Ballanpaf'. A description of the morphological and physiological characteristics of *Lantana camara* plant 'Ballanpaf' is presented below.

The following characteristics have been repeatedly observed and can be used to distinguish 'Ballanpaf' as a new and distinct cultivar of *Lantana camara* plant:

1. Deep yellow, medium orange, and deep reddish-purple multicolored inflorescences;
2. Dark green-colored foliage; and
3. Vigorous, trailing growth habit.

'Ballanpaf' has not been observed under all possible environmental conditions. Phenotype may vary due to environmental influence without variation in genotype. *Lantana camara* cultivar 'Ballanpaf' shows uniformity and stability within the limits of environmental influence for the traits described herein.

Color ratings were determined using the RHS Colour Chart of The Royal Horticultural Society of London (RHS), 2015 Edition, except where general color terms of ordinary significance are used. Color ratings were determined in August 2022 under natural light conditions in Naperville, Illinois. The following descriptions and measurements describe approximately 4.5-month-old plants produced from cuttings from stock plants and grown under conditions comparable to those used in commercial practice. Measurements and numerical values represent averages of typical plants. *These are typical values. Values may vary due to environment. Other values that are substantially equivalent are within the scope of the invention.

Botanical Classification: *Lantana camara* 'Ballanpaf'.

Parentage:

Female parent.—Proprietary *Lantana camara* breeding selection coded 18231, not patented.

Male parent.—BANDANA Landscape Red 'LANZ0015', U.S. Plant Pat. No. 29,653.

Propagation:

Type cutting.—Terminal stem.

Time to initiate roots.—Approximately 7 to 11 days.

Time to produce a rooted cutting.—Approximately 5 weeks.

Root description.—Fibrous.

Rooting habit.—Freely branching.

Plant Description:

Commercial crop time.—Approximately 6 to 7 weeks from a rooted cutting to finish in a 10 cm container.

Growth habit and general appearance.—Vigorous, trailing.

Size.—Height from soil level to top of plant plane: Approximately 21.0 cm. Height from lowest point to top of plant plane: Approximately 39.0 cm Width: Approximately 92.0 cm.

Branching habit.—Freely branching, pinching enhances branching. Quantity of branches per plant: Approximately 4 basal branches with 8 main lateral branches.

Lateral branch.—Shape: Square in cross section. Strength: Strong, becomes woody with age. Length: Approximately 43.0 cm. Diameter: Approximately 4.0 mm. Length of central internode: Approximately 4.5 cm. Texture: Densely pubescent with a mixture of glandular and nonglandular hairs. Gland color: Colorless, transparent. Color of young stem: 146B to 146C. Color of mature stem: 146B tinted with 187A, becomes woody 199A to 199B with age.

Foliage Description:

General description.—Quantity of leaves per lateral branch: Approximately 18. Fragrance: Strong, spicy. Form: Simple. Arrangement: Opposite.

Leaves.—Aspect: Perpendicular to obtuse angle to stem. Shape: Ovate. Margin: Serrate. Apex: Acute. Base: Obtuse. Venation pattern: Pinnate. Length of mature leaf: Approximately 5.2 cm. Width of mature leaf: Approximately 2.6 cm. Texture of upper surface: Moderately scabrous. Texture of lower surface: Densely pubescent with a mixture of scabrous and glandular hairs. Gland color: Colorless, transparent. Color of upper surface of young foliage: Closest to 137A with NN137A and venation of 146B to indistinguishable. Color of lower surface of young and mature foliage: Closest to 147B with venation of 146C. Color of upper surface of mature foliage: Closest to NN137A with venation of 146B to indistinguishable.

Petiole.—Length: Approximately 1.0 cm. Diameter: Approximately 2.0 mm. Texture: Moderately pubescent with a mixture of scabrous and glandular hairs. Gland color: Colorless, transparent. Color: 146B.

Flowering Description:

Flowering habit.—'Ballanpaf' is freely flowering under outdoor growing conditions with substantially continuous blooming from spring through autumn and year-round in greenhouse environment.

Lastingness of individual inflorescence on the plant.— Approximately 2 to 3 weeks.

Inflorescence Description:

General description.—Type: Hemispherical head, axillary or terminal. Quantity per plant: Approximately 120. Fragrance: Strong, spicy. Aspect: Primarily facing upward or outward. Height: Approximately 2.5 cm. Width: Approximately 3.5 cm. Quantity of fully open flowers per inflorescence: Approximately 34.

Peduncle.—Strength: Strong. Shape: Square in cross section. Aspect: Acute angle to stem. Length: Approximately 3.5 cm to 4.5 cm. Diameter: Approximately 2.0 mm. Texture: Densely pubescent with a mixture of glandular and nonglandular hairs. Gland color: Colorless, transparent. Color: 146B Flower Description:

General description.—Type: Salverform.

Bud.—Rate of opening: Generally takes 1 to 2 days for bud to progress from first color to fully open flower. Buds open in progression from the margin to the center of the inflorescence. Quantity of unopened inflorescences per plant: Approximately 20.

Bud just before opening.—Shape: Elongated, rectangular at apex. Length: Approximately 1.1 cm. Diameter: Approximately 3.0 mm. Color: N34B.

Corolla.—Depth: Approximately 1.5 cm. Diameter: Approximately 1.0 cm.

Petals.—Quantity: 4, non-imbricate, non-symmetrical petals. Petals are fused at base forming a corolla tube. Shape: Obovate. Appearance: Matte. Aspect: Flat to cupped. Margin: Entire, ruffled. Apex: Obtuse. Length of upper petal from throat: Approximately 4.0 mm. Width of upper petal: Approximately 6.0 mm. Length of lateral petals from throat: Approximately 3.0 mm. Width of lateral petals: Approximately 3.0 mm. Length of lower petal from throat: Approximately 5.0 mm.

Width of lower petal: Approximately 6.0 mm. Texture of upper surface: Glabrous. Texture of lower surface: Densely pubescent. Color of upper surface when first open: 12A. Color of lower surface when first open: 12C tinted with 25C. Color of upper surface when fully open: Transitions though 25B to NN78A, fading to N74D with age. Color of lower surface when fully open: N74C.

Corolla tube.—Length: Approximately 1.3 cm. Diameter at tube opening: Approximately 1.0 mm. Diameter at base: Approximately 1.0 mm. Texture of inner surface: Sparsely pubescent. Texture of outer surface: Densely pubescent at tube opening transitioning to glabrous at base. Color of pubescence N74A. Color of inner surface: NN155D with an underlay of N74C and base of 155C. Color of outer surface: N74C transitioning with age to N74D with base of 145D.

Calyx.—Shape: Tubular with two broadly acute tips. Length: Approximately 2.0 mm. Diameter: Approximately 1.5 mm. Texture of inner surface: Glabrous. Texture of outer surface: Densely pubescent. Color of inner and outer surfaces: 145D.

Bracts.—Quantity per flower: 1 per flower. Shape: Lanceolate. Length: Approximately 4.0 mm. Width: Approximately 1.0 mm. Texture of upper surface: Sparsely pubescent. Texture of lower surface: Densely pubescent. Color of upper surface: 145A with tip of 137A and base of 145D. Color of lower surface: 145B with tip of 137B and base of 145D.

Reproductive organs.—Androecium: Stamen quantity: 4, adnate to corolla tube. Stamen length: Approximately 2.0 mm. Anther shape: Bilobed, ovoid. Anther length: Approximately 1.0 mm. Anther color: 13B. Pollen amount: Sparse. Pollen color: 13D. Gynoecium: Pistil quantity: 1 per flower. Pistil length: Approximately 4.0 mm. Stigma shape: Funnel. Stigma length: Less than 1.0 mm. Stigma color: 144B. Style length: Approximately 3.0 mm. Style color: 155D, translucent. Ovary diameter: Approximately 1.0 mm. Ovary color: 144C.

C. Deposit Information

A deposit of representative sample of plant tissue of *Lantana camara* cultivar 'Ballanpaf' has been made with the Provasoli-Guillard National Center for Marine Algae and Microbiota (NCMA), 60 Bigelow Drive, East Boothbay, Maine, 04544 USA. The deposit was assigned NCMA Accession No. 202303016. The date of deposit of the representative sample of plant tissue with the NCMA was Mar. 17, 2023. The deposit has been accepted under the Budapest Treaty and will be maintained in the NCMA depository for a period of 30 years, or 5 years after the most recent request, or for the enforceable life of the patent, whichever is longer, and will be replaced if necessary during that period. Upon issuance, all restrictions on the availability to the public of the deposit will be irrevocably removed consistent with all of the requirements of the Budapest Treaty and 37 C.F.R. §§ 1.801-1.809. Applicant does not waive any infringement of rights granted under this patent or under the Plant Variety Protection Act (7 USC 2321 et seq.).

FURTHER EMBODIMENTS OF THE
INVENTION

A. Plant Breeding

In one aspect, the present disclosure provides plants modified using the methods described herein to include at least a first desired heritable trait. Such plants may, in one embodiment, be developed by backcrossing, wherein essentially all of the desired morphological and physiological characteristics of a cultivar are recovered in addition to a genetic locus transferred into the plant via the backcrossing technique. The term single locus converted plant as used herein refers to those plants which are developed by back-crossing or by genetic engineering, wherein essentially all of the desired morphological and physiological characteristics of a cultivar are recovered in addition to the single locus transferred into the cultivar via the backcrossing or genetic engineering technique, respectively. By essentially all of the desired morphological and physiological characteristics, it is meant that the characteristics of a plant are recovered that are otherwise present when compared in the same environment, other than an occasional variant trait that might arise during backcrossing, direct introduction of a transgene, or application of genetic engineering technique.

Backcrossing methods can be used with the present invention to improve or introduce a trait into a cultivar. The term backcrossing as used herein refers to the repeated crossing of a hybrid progeny back to one of the parental *Lantana camara* plants. The parental *Lantana camara* plant that contributes the locus or loci for the desired trait is termed the nonrecurrent or donor parent. This terminology refers to the fact that the nonrecurrent parent is used one time in the backcross protocol and therefore does not recur. The recurrent parent therefore provides the desired genetic background, while the choice of the particular nonrecurrent parent will depend on the purpose of the backcross. One of the major purposes is to add some commercially desirable trait to the plant. The exact backcrossing protocol will depend on the characteristic or trait being altered and the genetic distance between the recurrent and nonrecurrent parents. The present invention includes breeding methods comprising one or more backcrossing steps, wherein *Lantana camara* cultivar 'Ballanpaf' described herein can be used as the recurrent parent or the nonrecurrent parent. Although backcrossing methods are simplified when the characteristic being transferred is a dominant allele, a recessive allele or an additive allele (between recessive and dominant) may also be transferred. In this instance it may be necessary to introduce a test of the progeny to determine if the desired characteristic has been successfully transferred. The backcross process may be accelerated by the use of genetic markers, such as SSR, RFLP, SNP or AFLP markers to identify plants with the greatest genetic complement from the recurrent parent.

Modified backcrossing may also be used with the plants disclosed herein. This technique uses different recurrent parents during the backcrossing. Modified backcrossing may be used to replace the original recurrent parent with a variety having certain more desirable characteristics or multiple parents may be used to obtain different desirable characteristics from each.

With the development of molecular markers associated with particular traits, it is possible to add additional traits into an established germ line, such as represented here, with the end result being substantially the same base germplasm with the addition of a new trait or traits. Molecular breeding, as described in Moose and Mumm, 2008 (*Plant Physiol.*, 147: 969-977), for example, and elsewhere, provides a mechanism for integrating single or multiple traits or QTL into an elite line. This molecular breeding-facilitated movement of a trait or traits into an elite line may encompass incorporation of a particular genomic fragment associated with a particular trait of interest into the elite line by the mechanism of identification of the integrated genomic fragment with the use of flanking or associated marker assays.

In the embodiment represented here, one, two, three or four genomic loci, for example, may be integrated into an elite line via this methodology. When this elite line containing the additional loci is further crossed with another parental elite line to produce hybrid offspring, it is possible to then incorporate at least eight separate additional loci into the hybrid. In one embodiment, each locus may confer a separate trait. In another embodiment, loci may need to be homozygous and exist in each parent line to confer a trait in the hybrid. In yet another embodiment, multiple loci may be combined to confer a single robust phenotype of a desired trait.

Many traits have been identified that are not regularly selected for in the development of a new variety but that can be improved by backcrossing techniques. A genetic locus conferring the traits may or may not be transgenic. Examples of such traits known to those of skill in the art include, but are not limited to, herbicide tolerance, disease resistance, pest resistance, growth habit, fertility, and flower colors. These genes are generally inherited through the nucleus, but may be inherited through the cytoplasm.

Selection of *Lantana camara* plants for breeding is not necessarily dependent on the phenotype of a plant and instead can be based on genetic investigations. For example, one can utilize a suitable genetic marker which is closely genetically linked to a trait of interest. One of these markers can be used to identify the presence or absence of a trait in the offspring of a particular cross and can be used in selection of progeny for continued breeding. This technique is commonly referred to as marker assisted selection. Any other type of genetic marker or other assay which is able to identify the relative presence or absence of a trait of interest in a plant can also be useful for breeding purposes. Procedures for marker assisted selection are well known in the art. Such methods will be of particular utility in the case of recessive traits and variable phenotypes, or where conventional assays may be more expensive, time consuming, or otherwise disadvantageous. In addition, marker assisted selection may be used to identify plants comprising desirable genotypes at the seed, seedling, or plant stage, to identify or assess the purity of a cultivar, to catalog the genetic diversity of a germplasm collection, and to monitor specific alleles or haplotypes within an established cultivar.

Types of genetic markers which could be used in accordance with the invention include, but are not necessarily limited to, Simple Sequence Length Polymorphisms (SSLPs) (Williams et al., *Nucleic Acids Res.*, 1 8:6531-6535, 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., *Science*, 280:1077-1082, 1998).

In particular embodiments of the invention, marker assisted selection is used to increase the efficiency of a backcrossing breeding scheme for producing a *Lantana camara* line comprising a desired trait. This technique is commonly referred to as marker assisted backcrossing (MABC). This technique is well-known in the art and may involve, for example, the use of three or more levels of selection, including foreground selection to identity the presence of a desired locus, which may complement or replace phenotype screening protocols; recombinant selection to minimize linkage drag; and background selection to maximize recurrent parent genome recovery.

B. Breeding of *Lantana camara* Cultivar 'Ballanpaf'

One aspect of the invention concerns methods of crossing *Lantana camara* cultivar 'Ballanpaf' with itself or with any second plant. Such methods can be used for propagation of *Lantana camara* cultivar 'Ballanpaf', or can be used to produce plants that are derived from 'Ballanpaf'. Plants derived from *Lantana camara* cultivar 'Ballanpaf' may be used, in certain embodiments, for the development of new *Lantana* varieties.

Uniform lines of new varieties may also be developed by way of double-haploids. This technique allows the creation of true breeding lines without the need for multiple generations of selfing and selection. In this manner true breeding lines can be produced in as little as one generation. Haploid induction systems have been developed for various plants to produce haploid tissues, plants and seeds. The haploid induction system can produce haploid plants from any genotype by crossing with an inducer line. Inducer lines and methods for obtaining haploid plants are known in the art. Haploid embryos may be produced from microspores, pollen, anther cultures, or ovary cultures using techniques including, but not limited to, in vitro androgenesis or in vitro gynogenesis. The haploid embryos may then be doubled autonomously, or by chemical treatments (e.g., colchicine treatment). Alternatively, haploid embryos may be grown into haploid plants and treated to induce chromosome doubling. In either case, fertile homozygous plants are obtained. In accordance with the invention, any of such techniques may be used in connection with a plant of the invention and progeny thereof to achieve a homozygous line.

In one aspect, microspore-derived haploid embryos can be converted to doubled haploid embryos through the use of chromosome doubling agents or through spontaneous doubling. As used herein the term "microspore-derived embryo" refers to an embryo that was derived from microspore through tissue culture. As used herein the term "tissue culture" refers to composition comprising isolated cells of the same or of a different type or a collection of such cells organized into parts of a plant. Exemplary types of tissue cultures are protoplasts, calli, and plant cells that are intact in plants or parts of plants, such as embryos, pollen, flowers, leaves, roots, root tips, anthers, and the like. Means for preparing and maintaining plant tissue cultures are well known in the art (U.S. Pat. Nos. 5,538,880; 5,550,318; 5,445,961 and 5,322,789), the entire disclosure each of which is incorporated herein by reference.

In certain aspects, a method of chromosome doubling provided herein comprises the use of colchicine. Colchicine may be used at concentrations of about 25 mg/L to about 1600 mg/L, however preferably at a concentration of about 200 mg/L to about 1000 mg/L. When colchicine is used, microspores are treated preferably at a temperature of about 32° C. for a duration of about 24 hours to about 72 hours. Colchicine may be substituted with any other doubling agent known in the art. Non-limiting examples of which include amiprophos-methyl, oryzalin, pronamide, and trifluralin. As used herein, when referring to chromosome count, "doubling" refers to increasing the chromosome number by a factor of two. For example, a haploid nuclear genome comprising 10 chromosomes is doubled to become a diploid nuclear genome comprising 20 chromosomes. As another example, a diploid nuclear genome comprising 20 chromosomes is doubled to become a tetraploid nuclear genome comprising 40 chromosomes. Chromosome doubling can be confirmed by flow cytometry or other molecular biology techniques known in the art.

The development of new varieties using one or more starting varieties is well known in the art and encompassed by the disclosure. In accordance with the disclosure, novel varieties may be created by crossing a plant of the disclosure followed by multiple generations of breeding according to such well-known methods. New varieties may be created by crossing with any second plant. New varieties may be developed, for example, by applying a breeding technique to a plant of *Lantana camara* cultivar 'Ballanpaf'. Such breeding techniques are well-known in the art and include but are not limited to recurrent selection, mass selection, hybridization, open-pollination, backcrossing, modified backcrossing, endosperm culture, pedigree breeding, mutation breeding, and marker assisted selection. "Mutation breeding" as used herein refers to a breeding technique comprising selecting a naturally occurring (spontaneous) mutation or inducing a mutation through means such as irradiation or chemical induction. *Lantana camara* plants produced by applying breeding techniques to a plant of *Lantana camara* cultivar 'Ballanpaf' may for example have a inflorescence color that is different from that of *Lantana camara* cultivar 'Ballanpaf'. Non-limiting examples of flower colors that may be produced by applying breeding techniques to a plant of *Lantana camara* cultivar 'Ballanpaf' include white, yellow, yellow-orange, orange, red-orange, red, purplish-red, purplish-pink, reddish-purple, purple, and combinations of any thereof.

In selecting a second plant to cross with a plant of the disclosure, it will typically be preferred to choose those plants which either themselves exhibit one or more selected desirable characteristics or which exhibit the desired characteristic(s) when in hybrid combination. Once initial crosses have been made, selection takes place to produce new varieties. Examples of desirable traits may include, in specific embodiments, flower color or size, color patterning, foliage quality, growth habit, shape and uniformity, maturity date, flower yield, seed germination rate, seedling vigor, pest and disease resistance, herbicide tolerance, and adaptability for soil and climate conditions. Consumer-driven traits are other traits that may be incorporated into new plants developed by this disclosure.

One aspect of the current disclosure therefore provides methods for producing a *Lantana camara* plant comprising multicolored inflorescences, dark green-colored foliage, and a vigorous, trailing growth habit. In certain embodiments, the method may comprise (a) producing a *Lantana camara* cultivar 'Ballanpaf'-derived *Lantana camara* plant from a seed produced by crossing a plant of *Lantana camara* cultivar 'Ballanpaf' with itself or a second *Lantana camara* plant; (b) crossing the *Lantana camara* cultivar 'Ballanpaf'-derived *Lantana camara* plant with itself or a different *Lantana camara* plant to obtain a seed of a further *Lantana camara* cultivar 'Ballanpaf'-derived *Lantana camara* plant; (c) selecting a further *Lantana camara* cultivar 'Ballanpaf'-derived *Lantana camara* plant that comprises multicolored inflorescences comprising white, yellow, yellow-orange, orange, red-orange, red, purplish-red, purplish-pink, reddish-purple, or purple flowers, dark green-colored foliage, and a vigorous, trailing growth habit; (d) repeating said producing, crossing, and selecting steps of (a), (b), and (c) using the seed of said step (b) for at least one generation to produce a seed an additional 'Ballanpaf'-derived *Lantana camara* plant; and (c) selecting an additional *Lantana camara* cultivar 'Ballanpaf'-derived *Lantana camara* plant comprising multicolored inflorescences comprising white, yellow, yellow-orange, orange, red-orange, red, purplish-red, purplish-pink, reddish-purple, or purple flowers, dark green-colored foliage, and a vigorous, trailing growth habit. In a particular embodiment, the second plant may be a *Lantana camara* plant and the progeny seed may be planted and grown to produce fertile hybrid progeny plants. A plant in accordance with the disclosure may be used in such crosses as the female plant or the male plant.

The disclosure also provides methods of producing *Lantana camara* plants derived from *Lantana camara* cultivar 'Ballanpaf'. The method may comprise (a) crossing a *Lantana camara* plant of *Lantana camara* cultivar 'Ballanpaf' with itself or a second plant capable of being crossed thereto; and (b) collecting resulting seed. In one embodiment, the second plant may be a *Lantana camara* plant. In some embodiments, the methods of the present disclosure may further comprise the step of (c) crossing a plant grown from said seed of step (b) with itself or a second plant at least one or more additional time(s) to yield additional seed. Plants, seeds, and plant parts produced from the methods described herein and plants comprising multicolored inflorescences, dark green-colored foliage, or a vigorous, trailing growth habit as described herein are also provided.

In certain embodiments, hybrid seeds may be produced using the methods of the present disclosure. A parent plant of such a seed may be a *Lantana camara* plant of *Lantana camara* cultivar 'Ballanpaf'. In other embodiments, a plant as described herein may be either the male plant or the female plant in a given cross.

In accordance with the disclosure, any species of lantana may be used. In particular, *Lantana camara* species that may be useful include but are not limited to *Lantana camara*, *Lantana montevidensis*, *Lantana involucrata*, *Lantana trifolia*, *Lantana urticoides*, *L. depressa*, *L. hirsuta*, *L. horrida*, *L. splendens*, *L. strigocamara*, *Lantana achyranthifolia*, and the like.

C. Plants Derived by Genetic Engineering

Various genetic engineering technologies have been developed and may be used by those of skill in the art to introduce traits in plants. In certain aspects of the claimed invention, traits are introduced into *Lantana camara* plants via altering or introducing a single genetic locus or transgene into the genome of a recited variety or progenitor thereof. Methods of genetic engineering to modify, delete, or insert genes and polynucleotides into the genomic DNA of plants are well-known in the art.

In specific embodiments of the invention, improved *Lantana camara* cultivars can be created through the site-specific modification of a plant genome. Methods of genetic engineering include, for example, utilizing sequence-specific nucleases such as zinc-finger nucleases (see, for example, U.S. Pat. Appl. Pub. No. 2011-0203012); engineered or native meganucleases; TALE-endonucleases (see, for example, U.S. Pat. Nos. 8,586,363 and 9,181,535); and RNA-guided endonucleases, such as those of the CRISPR/Cas systems (see, for example, U.S. Pat. Nos. 8,697,359 and 8,771,945 and U.S. Pat. Appl. Pub. No. 2014-0068797). One embodiment of the invention thus relates to utilizing a nuclease or any associated protein to carry out genome modification. This nuclease could be provided heterologously within donor template DNA for templated-genomic editing or in a separate molecule or vector. A recombinant DNA construct may also comprise a sequence encoding one or more guide RNAs to direct the nuclease to the site within the plant genome to be modified. Further methods for altering or introducing a single genetic locus include, for example, utilizing single-stranded oligonucleotides to introduce base pair modifications in a *Lantana camara* plant genome (see, for example Sauer et al., *Plant Physiol,* 170(4): 1917-1928, 2016).

Methods for site-directed alteration or introduction of a single genetic locus are well-known in the art and include those that utilize sequence-specific nucleases, such as the aforementioned, or complexes of proteins and guide-RNA that cut genomic DNA to produce a double-strand break (DSB) or nick at a genetic locus. As is well-understood in the art, during the process of repairing the DSB or nick introduced by the nuclease enzyme, a donor template, transgene, or expression cassette polynucleotide may become integrated into the genome at the site of the DSB or nick. The presence of homology arms in the DNA to be integrated may promote the adoption and targeting of the insertion sequence into the plant genome during the repair process through homologous recombination or non-homologous end joining (NHEJ).

In another embodiment of the invention, genetic transformation may be used to insert a selected transgene into a plant of the disclosure or may, alternatively, be used for the preparation of transgenes which can be introduced by backcrossing. Methods for the transformation of plants that are well known to those of skill in the art and applicable to many plant species include, but are not limited to, electroporation, microprojectile bombardment, *Agrobacterium*-mediated transformation and direct DNA uptake by protoplasts.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

An efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large. Microprojectile bombardment techniques are widely applicable, and may be used to transform virtually any plant species.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations. Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (U.S. Pat. No. 5,563,055, incorporated herein by reference in its entirety). Transformation of plant protoplasts also can be achieved using methods based on calcium phosphate precipitation, polyethylene glycol treatment, electroporation, and combinations of these treatments.

A number of promoters have utility for plant gene expression for any gene of interest including but not limited to selectable markers, scoreable markers, genes for pest and disease resistance, and any other gene of agronomic interest. Examples of constitutive promoters useful for driving gene expression in plants include, but are not limited to, the cauliflower mosaic virus (CaMV) P-35S promoter, which confers constitutive, high-level expression in most plant tissues, including monocots; a tandemly duplicated version of the CaMV 35S promoter, the enhanced 35S promoter (P-e35S) the nopaline synthase promoter, the octopine synthase promoter; and the figwort mosaic virus (P-FMV) promoter as described in U.S. Pat. No. 5,378,619 (incorporated herein by reference in its entirety), and an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, and other plant DNA virus promoters known to express in plant cells.

A variety of plant gene promoters that are regulated in response to environmental, hormonal, chemical, and/or developmental signals can be used for expression of an operably linked gene in plant cells, including promoters regulated by (1) heat, (2) light (e.g., pea rbcS-3A promoter; maize rbcS promoter; or chlorophyll a/b-binding protein promoter), (3) hormones, such as abscisic acid, (4) wounding (e.g., wunl); or (5) chemicals such as methyl jasmonate, salicylic acid, or Safener. It may also be advantageous to employ organ-specific promoters.

Exemplary nucleic acids which may be introduced to the plants of this disclosure include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a plant of *Lantana camara* cultivar 'Ballanpaf'. Non-limiting examples of particular genes and corresponding phenotypes one may choose to introduce into a of the disclosure include one or more genes for insect tolerance, such as a *Bacillus thuringiensis* (B.t.) gene, pest tolerance such as genes for fungal disease control, herbicide tolerance such as genes conferring glyphosate tolerance, and genes for quality improvements such as environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, U.S. Pat. Nos. 5,689,052, 5,500,365 and 5,880,275, each of which are herein incorporated by reference in their entirety. In another embodiment, the structural gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Alternatively, the DNA coding sequences can affect these phenotypes by encoding a non-translatable RNA molecule that causes the targeted inhibition of expression of an endogenous gene, for example via antisense- or co-suppression-mediated mechanisms. The RNA could also be a catalytic RNA molecule (i.e., a ribozyme) engineered to cleave a desired endogenous mRNA product. Thus, any gene which produces a protein or mRNA which expresses a phenotype or morphology change of interest is useful for the practice of the present disclosure.

D. Genetic Complements

In another aspect of the invention, the genetic complement of the *Lantana camara* plant cultivar designated 'Ballanpaf' is provided. The phrase "genetic complement" is used to refer to the aggregate of nucleotide sequences, the expression of which sequences defines the phenotype of, in the present case, a *Lantana camara* plant, or a cell or tissue of that plant. A genetic complement thus represents the genetic makeup of cell, tissue or plant, and a hybrid genetic complement represents the genetic makeup of a hybrid cell, tissue or plant. The invention thus provides *Lantana camara* plant cells that have a genetic complement in accordance with the *Lantana camara* plant cells disclosed herein, and plants, seeds and polyploid plants containing such cells.

Plant genetic complements may be assessed by genetic marker profiles, and by the expression of phenotypic traits that are characteristic of the expression of the genetic complement, e.g., isozyme typing profiles. It is understood that cultivar 'Ballanpaf' could be identified by any of the many well-known techniques such as, for example, Simple Sequence Length Polymorphisms (SSLPs) (Williams et al., *Nucleic Acids Res.,* 18:6531-6535, 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., *Science,* 280:1077-1082, 1998).

In yet another aspect, the present invention provides hybrid genetic complements, as represented by *Lantana camara* plant cells, tissues, plants, and seeds, formed by the combination of a haploid genetic complement of a *Lantana camara* plant of the invention with a haploid genetic complement of the same or a different cultivar. In another aspect, the present invention provides a *Lantana camara* plant regenerated from a tissue culture that comprises a hybrid genetic complement of this invention.

E. Additional Traits

Additional traits can be introduced into the *Lantana camara* cultivar of the present invention. A non-limiting example of such a trait is a coding sequence that decreases RNA and/or protein levels. The decreased RNA and/or protein levels may be achieved through RNAi methods, such as those described in U.S. Pat. No. 6,506,559 to Fire and Mellow.

Another trait that may find use with the *Lantana camara* cultivar of the invention is a sequence that allows for site-specific recombination. Examples of such sequences include the FRT sequence, used with the FLP recombinase (Zhu and Sadowski, *J. Biol. Chem.,* 270:23044-23054, 1995); and the LOX sequence, used with CRE recombinase (Sauer, *Mol. Cell. Biol.,* 7:2087-2096, 1987). The recombinase genes can be encoded at any location within the genome of the *Lantana camara* plant, and are active in the hemizygous state.

It may also be desirable to make *Lantana camara* plants more tolerant to or more easily transformed with *Agrobacterium tumefaciens.* Expression of p53 and iap, two baculovirus cell-death suppressor genes, inhibited tissue necrosis and DNA cleavage. Additional targets can include plant-encoded proteins that interact with the *Agrobacterium* Vir genes; enzymes involved in plant cell wall formation; and histones, histone acetyltransferases and histone deacetylases (reviewed in Gelvin, *Microbiology & Mol. Biol. Reviews,* 67:16-37, 2003).

F. Plants Comprising Non-Transgenic Mutations

In still yet another aspect, a plant of *Lantana camara* cultivar designated 'Ballanpaf', further comprising a non-transgenic mutation is provided. The phrase "non-transgenic mutation" is used herein to refer to a mutation that is naturally occurring (spontaneous), or induced by conventional methods (e.g. exposure of plants to radiation or mutagenic compounds), not including mutations made using recombinant DNA techniques. Various mutagenesis techniques have been developed and may be used by those of skill in the art to induce mutations in plants. Methods of mutagenesis may include, for example, exposure to irradiation, mutagenic compounds, extreme heat, or tissue culture conditions; long-term seed storage; and targeting induced local lesions in genomes (TILLING). In some embodiments, ionizing radiation may be produced by X-rays, gamma rays, neutrons, beta rays, or ultraviolet rays. Non-limiting examples of chemical mutagens include base analogues, antibiotics, alkylating agents, sodium azide, hydroxylamine, nitrous acid, methylnitrilsourea, and acridines. Methods of mutagenesis to modify, delete, or insert polynucleotides into the genomic DNA are well-known in the art.

In one aspect, improved *Lantana camara* cultivars may be created through mutation of the plant genome. In one embodiment, a plant of the *Lantana camara* cultivar 'Ballanpaf' may be subjected to a mutagenesis technique to create a population of mutant plants. Such mutant plants, for example, may comprise a mutation and otherwise comprise all of the physiological and morphological characteristics of *Lantana camara* cultivar 'Ballanpaf'. In particular embodiments, mutant plants may comprise a mutation and otherwise comprise all of the morphological and physiological characteristics of *Lantana camara* cultivar 'Ballanpaf' with the exception of flower color or plant height. Mutant plants of *Lantana camara* cultivar 'Ballanpaf' may, for example, have inflorescences with flower colors including, but not limited to, shades of white, yellow, yellow-orange, orange, red-orange, red, purplish-red, purplish-pink, reddish-purple, and purple. Mutant plants of *Lantana camara* cultivar 'Ballanpaf' may exhibit foliage that is lighter green or darker green than wild-type 'Ballanpaf'. Mutant plants of *Lantana camara* cultivar 'Ballanpaf' may also exhibit a trailing growth habit that is less vigorous or more vigorous than wild-type 'Ballanpaf'.

G. Tissue Cultures and In Vitro Regeneration of *Lantana camara* Plants

In one aspect, the invention relates to tissue cultures of the *Lantana camara* plant designated 'Ballanpaf'. As used herein, the term "tissue culture" indicates a composition comprising isolated cells of the same or a different type or a collection of such cells organized into parts of a plant. Exemplary types of tissue cultures are protoplasts, calli and plant cells that are intact in plants or parts of plants, such as embryos, meristems, cotyledons, pollen, leaves, anthers, roots, root tips, pistils, flowers, cuttings, seeds, and stems, and the like. In a preferred embodiment, the tissue culture comprises cells derived from immature tissues of these plant parts. Means for preparing and maintaining plant tissue cultures are well known in the art (Abbasi, et al., *In Vitro Cell Dev. Biol.—Plant,* 43:481-492, 2007, and Parsons, et al., *Pharm. Biol.,* 56(1): 485-494, 2018, each incorporated herein by reference in their entirety).

In another aspect, the present disclosure provides *Lantana camara* cultivar 'Ballanpaf'-derived plants produced using endosperm culture techniques. In angiosperms, such as the Verbenaceae family, the endosperm is the main nutritive tissue for the embryo. The endosperm is the product of double fertilization wherein one male gamete fertilizes the egg to form zygote, and the other fuses with secondary nuclei to form triploid endosperm. Endosperm culture is a useful procedure for the production of triploids from diploid plants. In addition to conventional polyploid production by chemical treatment, endosperm culture can be incorporated into polyploid breeding programs. By using tissue culture techniques, one can regenerate triploid plants from the endosperm. Both mature and immature endosperm can be used for endosperm culture initiation.

In yet another aspect, compositions are provided comprising a cell of *Lantana camara* cultivar 'Ballanpaf' comprised in plant cell growth media. Plant cell growth media are well known to those of skill in the art, e.g. Veraplakorn et al., *Agriculture and Natural Resources* (2016), 50(5); 338-344; specifically incorporated herein by reference). Plant cell growth media can provide adequate support for plant cells, including providing moisture and/or nutritional components.

H. Processes of Crossing *Lantana camara* Plants and the *Lantana camara* Plants Produced by Such Crosses The present invention provides processes of preparing novel *Lantana camara* plants and *Lantana camara* plants produced by such processes. In accordance with such a process, a first parent *Lantana camara* plant may be crossed with a second parent *Lantana camara* plant wherein at least one of the first and second *Lantana camara* plants is the *Lantana camara* plant 'Ballanpaf'. One application of the process is in the production of $F_1$ hybrid plants. Another important aspect of this process is that it can be used for the development of novel cultivars. For example, the *Lantana camara* plant 'Ballanpaf' could be crossed to any second plant, and the resulting hybrid progeny could be vegetatively propagated or the hybrid progeny could be each selfed for about 5 to 7 or more generations, thereby providing a large number of distinct cultivars. These cultivars could then be crossed with other cultivars and the resulting hybrid progeny analyzed for beneficial characteristics. In this way, novel cultivars conferring desirable characteristics could be identified. "Vegetative propagation" as used herein refers to any form of asexual reproduction occurring in plants in which a new plant grows from a fragment of the parent plant. Non-limiting examples of vegetative propagation methods include tissue culture and division.

I. $F_1$ Hybrid *Lantana camara* Plant and Seed Production

One beneficial use of the instant *Lantana camara* cultivar is in the production of hybrid seed. Any time the *Lantana camara* plant 'Ballanpaf' is crossed with another, different, *Lantana camara* plant, a first generation ($F_1$) *Lantana camara* hybrid plant is produced. As such, an $F_1$ hybrid *Lantana camara* plant can be produced by crossing 'Ballanpaf' with any second *Lantana camara* plant. Essentially any other *Lantana* plant can be used to produce a hybrid *Lantana* plant having *Lantana camara* plant 'Ballanpaf' as one parent. All that is required is that the second plant be fertile, which *Lantana camara* plants naturally are, and that the plant is not *Lantana camara* cultivar 'Ballanpaf'.

The goal of the process of producing an $F_1$ hybrid is to manipulate the genetic complement of *Lantana camara* to generate new combinations of genes that interact to yield new or improved traits (phenotypic characteristics).

*Lantana camara* plants have been found to exhibit varying ploidy levels, including diploid, triploid, tetraploid, pentaploid, and hexaploidy. In diploid *Lantana camara* plants, two conditions of a gene (two alleles) occupy each locus (position on a chromosome). If the alleles are the same at a locus, there is said to be homozygosity. If they are different, there is said to be heterozygosity.

Hundreds of *Lantana* varieties are known to those of skill in the art, any one of which could be crossed with *Lantana camara* plant 'Ballanpaf' to produce a hybrid plant. For example, the U.S. Patent & Trademark Office has issued more than 100 plant patents for *Lantana* varieties.

When the *Lantana camara* plant 'Ballanpaf' is crossed with another *Lantana* plant to yield a hybrid, it can serve as either the maternal or paternal plant. For many crosses, the outcome is the same regardless of the assigned sex of the parental plants. Depending on the seed production characteristics relative to a second parent in a hybrid cross, it may be desired to use one of the parental plants as the male or female parent. Seed coat characteristics can be preferable in one plant. Pollen can be shed better by one plant. Therefore, a decision to use one parent plant as a male or female may be made based on any such characteristics as is well known to those of skill in the art.

J. Development of *Lantana camara* Varieties

The development of new varieties using one or more starting varieties is well known in the art. In accordance with the invention, novel varieties may be created by crossing *Lantana camara* cultivar 'Ballanpaf' followed by vegetative propagation of selected plants. In certain embodiments, novel varieties may be created by crossing *Lantana camara* cultivar 'Ballanpaf' followed by multiple generations of breeding according to such well-known methods. New varieties may be created by crossing *Lantana camara* cultivar 'Ballanpaf' with any second plant. In selecting such a second plant to cross for the purpose of developing novel varieties, it may be desired to choose those plants that either themselves exhibit one or more selected desirable characteristics or exhibit the desired characteristic(s) when in hybrid combination. Examples of potentially desired characteristics include flower color or size, color patterning, foliage quality, growth habit, shape and uniformity, maturity date, flower yield, fertility, sterility, seed germination rate, seedling vigor, pest and disease resistance, and adaptability for soil and climate conditions.

Once initial crosses have been made with *Lantana camara* cultivar 'Ballanpaf', vegetative propagation or inbreeding takes place to produce new varieties. Inbreeding requires manipulation by human breeders. Even in the extremely unlikely event inbreeding rather than crossbreeding occurred in natural *Lantana camara*, achievement of complete inbreeding cannot be expected in nature due to well-known deleterious effects of homozygosity and the large number of generations the plant would have to breed in isolation. The reason for the breeder to create inbred plants is to have a known reservoir of genes whose gametic transmission is predictable.

The pedigree breeding method involves crossing two genotypes. Each genotype can have one or more desirable characteristics lacking in the other; or, each genotype can complement the other. If the two original parental genotypes do not provide all of the desired characteristics, other genotypes can be included in the breeding population. Superior plants that are the products of these crosses are selfed and selected in successive generations. Each succeeding generation becomes more homogeneous as a result of self-pollination and selection. Typically, this method of breeding involves five or more generations of selfing and selection: $S_1 \rightarrow S_2$; $S_2 \rightarrow S_3$; $S_3 \rightarrow S_4$; $S_4 \rightarrow S_5$, etc. After at least five generations, the inbred plant is considered genetically pure.

EXAMPLES

Example 1-Distinguishing Characteristics of
*Lantana camara* Cultivar 'Ballanpaf'

The most similar, commercially available *Lantana camara* cultivar to 'Ballanpaf' is Bandolista 'Mango' (not patented). However, 'Ballanpaf' can be distinguished from 'Mango' at least based upon the increased trailing growth habit of 'Ballanpaf'; and distinct inflorescence coloring in comparison to Bandolista 'Mango'. Specifically, *Lantana camara* cultivar 'Ballanpaf' exhibits a deeper purplish-pink inflorescence color as compared to 'Mango'.

Example 2-Plants Produced from *Lantana camara*
Cultivar 'Ballanpaf'

The present invention provides *Lantana camara* plants derived from the *Lantana camara* plant 'Ballanpaf', e.g. $F_1$ hybrid *Lantana camara* plants derived from 'Ballanpaf'. *Lantana camara* plants derived from the *Lantana camara* plant 'Ballanpaf' may comprise inflorescences having flower colors including, but not limited to, white, yellow, yellow-orange, orange, red-orange, red, purplish-red, purplish-pink, reddish-purple, purple, and combinations of any thereof. In particular, *Lantana camara* plants derived from the *Lantana camara* plant 'Ballanpaf' will be produced using the methods known in the art. For example, $F_1$ hybrid *Lantana camara* plant will be produced by crossing 'Ballanpaf' with a second *Lantana camara* plant to produce a hybrid *Lantana* plant having *Lantana camara* plant 'Ballanpaf' as one parent.

Additionally, *Lantana camara* plants derived from the *Lantana camara* plant 'Ballanpaf' may also be produced from a tissue culture of regenerable cells of *Lantana camara* cultivar 'Ballanpaf'. Regenerable cells of 'Ballanpaf', for example, cells derived from embryos, meristems, cotyledons, pollen, endosperm, leaves, anthers, roots, root tips, pistils, flowers, cuttings, seeds, and stems will be used to produce *Lantana camara* plants regenerated from the tissue culture. Such *Lantana camara* cultivar 'Ballanpaf'-derived plants will then be selected based upon one or more desirable characteristics, e.g. flower coloration, foliage color, or growth habit.

In particular, *Lantana camara* cultivar 'Ballanpaf'-derived plants will be produced using genetic engineering, induced mutation, or spontaneous mutation.

All of the compositions and methods disclosed and claimed herein can be made and executed without undue experimentation in light of the present disclosure. While the compositions and methods of this invention have been described in terms of the foregoing illustrative embodiments, it will be apparent to those of skill in the art that variations, changes, modifications, and alterations may be applied to the composition, methods, and in the steps or in the sequence of steps of the methods described herein, without departing from the true concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

The references cited herein, to the extent that they provide exemplary procedural or other details supplementary to those set forth herein, are specifically incorporated herein by reference.

What is claimed is:

1. A *Lantana camara* plant of cultivar 'Ballanpaf', a representative sample of plant tissue of said cultivar having been deposited under NCMA Accession No. 202303016.

2. A seed of the plant of claim 1.

3. A plant part of the plant of claim 1, wherein said plant part comprises at least one cell of said plant.

4. The plant part of claim 3, defined as a flower, pollen, a leaf, an ovule, an embryo, a cutting, an axillary bud, a stem, or a seed.

5. A *Lantana camara* plant having all of the physiological and morphological characteristics of the plant of claim 1.

6. A tissue culture of regenerable cells of the plant of claim 1.

7. A *Lantana camara* plant regenerated from the tissue culture of claim 6, wherein said plant comprises all of the physiological and morphological characteristics of the plant of claim 1.

8. A method of vegetatively propagating a *Lantana camara* plant comprising the steps of:
(a) collecting tissue from the plant of claim 1; and
(b) vegetatively propagating a plant from said tissue.

9. A *Lantana camara* plant produced by the method of claim 8, wherein said plant comprises all of the physiological and morphological characteristics of the plant of claim 1.

10. A method of producing a *Lantana camara* plant comprising an added trait, the method comprising introducing a transgene conferring the trait into the plant of claim 1.

11. A *Lantana camara* plant produced by the method of claim 10.

12. The plant of claim 1, wherein said plant further comprises a transgene, and wherein said plant otherwise comprises all of the physiological and morphological characteristics of the plant of claim 1.

13. The plant of claim 1, wherein said plant further comprises a single locus conversion, and wherein said plant otherwise comprises all of the physiological and morphological characteristics of the plant of claim 1.

14. The plant of claim 1, wherein said plant further comprises a non-transgenic mutation, and wherein said plant otherwise comprises all of the physiological and morphological characteristics of the plant of claim 1.

15. The plant of claim 14, wherein the non-transgenic mutation confers white, yellow, yellow-orange, orange, red-orange, red, purplish-red, purplish-pink, reddish-purple, or purple flower color.

16. A method of plant breeding comprising applying plant breeding techniques to a plant according to claim 1.

17. The method of claim 16, defined as comprising producing a *Lantana camara* cultivar 'Ballanpaf'-derived *Lantana camara* plant.

18. The method of claim 16, wherein said plant breeding techniques comprise recurrent selection, mass selection, hybridization, open-pollination, backcrossing, modified backcrossing, endosperm culture, pedigree breeding, mutation breeding, or marker assisted selection.

19. The method of claim 17, further defined as comprising selecting a *Lantana camara* cultivar 'Ballanpaf'-derived *Lantana camara* plant that comprises a trailing growth habit found in *Lantana camara* cultivar 'Ballanpaf'.

20. A *Lantana camara* plant produced by the method of claim 16, wherein said plant comprises dark green colored foliage, and a trailing growth habit and has inflorescence comprising white, yellow, yellow-orange, orange, red-orange, red, purplish-red, purplish-pink, reddish-purple, or purple flowers, and wherein said plant otherwise comprises all of the physiological and morphological characteristics of the plant of claim 1.

21. A method of obtaining a *Lantana camara* plant with a trailing growth habit comprising producing a progeny plant of a plant according to claim 1.

22. A method of introducing a trailing growth habit into a Lantana plant, the method comprising the steps of:
(a) crossing a plant of *Lantana camara* cultivar 'Ballanpaf' according to claim 1 with a second Lantana plant to produce $F_1$ progeny;
(b) selecting an $F_1$ progeny that comprises the trailing growth habit found in *Lantana camara* cultivar 'Ballanpaf';
(c) backcrossing the selected $F_1$ progeny with the second Lantana plant to produce backcross progeny; and
(d) repeating steps (b) and (c) three or more times to produce a selected fourth or higher backcross progeny that comprises the trailing growth habit found in *Lantana camara* cultivar 'Ballanpaf'.

23. A plant produced by the method of claim 22, wherein said plant comprises all of the physiological and morphological characteristics of the plant of claim 1.

24. A method for producing a *Lantana camara* plant comprising vegetatively propagating a *Lantana camara* plant comprising a trailing growth habit found in *Lantana camara* cultivar 'Ballanpaf', wherein said plant is the product of applying a plant breeding technique to the plant of claim 1.

25. A plant produced by the method of claim 24, wherein said plant comprises all of the physiological and morphological characteristics of the plant of claim 1.

\*  \*  \*  \*  \*